(12) United States Patent
Hsu (10) Patent No.: US 6,193,868 B1
(45) Date of Patent: Feb. 27, 2001

(54) ELECTROPHORETIC SEPARATING AND BLOTTING APPARATUS

(76) Inventor: Yi-Hua Hsu, No. 11, Alley 22, Lane 95, Chung-Shan 1st Rd., Lu-Chou, Taipei (TW)

( * ) Notice: Subject to any disclaimer, the term of this patent is extended or adjusted under 35 U.S.C. 154(b) by 0 days.

(21) Appl. No.: 09/397,087

(22) Filed: Sep. 16, 1999

(51) Int. Cl.$^7$ .................................................. G01N 27/26
(52) U.S. Cl. ......................... 204/618; 204/614; 249/165
(58) Field of Search .................................. 204/605, 614, 204/616, 618, 619, 620; 249/163, 160, 165; 422/101

Primary Examiner—Jill Warden
Assistant Examiner—Alex Noguerola
(74) Attorney, Agent, or Firm—Bacon & Thomas, PLLC (57) ABSTRACT

An electrophoretic separating and blotting apparatus, which includes a pressure block, two glass plates of different heights, a partition frame, a rack, a positioning unit, a cell, a blotting cassette, and two electrode plates. The component parts are alternatively used for electrophoretic gelation as well as blotting, enabling electrophoretic gelation process and blotting process to be efficiently and economically proceeded within a short length of time.

3 Claims, 15 Drawing Sheets

ELECTROPHORETIC SEPARATING AND BLOTTING APPARATUS

BACKGROUND OF THE INVENTION

The present invention relates to an electrophoretic separating and blotting apparatus, and more particularly to such an apparatus, which is practical for use in electrophoretic gelation process, as well as blotting process.

Electrophoresis is a technique commonly used to separate protein and DNA. According to conventional methods, a gel is cast between two plates (in vertical) or on a flat bed (in horizontal), and inserted in between buffer/electrode chambers in an electrophoretic apparatus. A buffer solution is added to the buffer/electrode chambers, and a small amount of sample solution is loaded in wells in the gel. Glycerin and "tracing" dye are put in the wells or added to the sample solution. An electric current is then given to the gel. After tracing dye has been run through the length of the gel, the electric current is stopped, and the gel is removed from the apparatus for analysis to measure the transfer of the molecules of the sample. The gel can be colored by, for example, a dye, enabling the dye to be bonded to protein or DNA. The gel can then be dried, preserved, or photographed, enabling the distribution of the molecules of the sample to be recorded for permanent visual check. After electrophoresis, the gel must be taken out of the electrophoretic apparatus, and then delivered to a blotting apparatus for blotting. Because the electrophoretic apparatus and the blotting apparatus are two independent apparatus, they must be separately prepared. Because the electrophoretic procedure and the blotting procedure must be performed separately in the electrophoretic apparatus and the blotting apparatus, it is complicated and time-consuming to achieve electrophoretic and blotting operations.

SUMMARY OF THE INVENTION

The present invention has been accomplished to provide an electrophoretic separating and blotting apparatus, which eliminates the aforesaid drawbacks. It is the main object of the present invention to provide an electrophoretic separating and blotting apparatus, which can be arranged into different modes for running an electrophoretic process as well as a blotting procedure economically and efficiently.

DETAILED DESCRIPTION OF THE PREFERRED EMBODIMENT

An electrophoretic gel separation method is a technique commonly used to separate protein and DNA. Charge carried molecules are movable under the guide of an electric field. By means of the porous nature of a gel and under the driving of an electric field, molecules are separated or arranged subject to the order of molecular size. Electrophoresis includes the steps of gelation (alignment, casting), sample-loading, and running. The performance of one step affects the success of a next step.

Referring to FIGS. from 1 through 6, an electrophoretic separating an blotting apparatus in accordance with the present invention comprises a pressure block 1, two glass plates 11 and 11', two spacers 12, a comb 13, a partition frame 2, a rack 3, a positioning unit 4, a cell 5, a transfer membrane 7, two pieces of filter paper 8, a blotting cassette 9, and two plate electrodes 10 and 10'.

The glass plates 11 and 11' have different heights. The spacers 12 and 12' are bilaterally arranged between the glass plates 11 and 11'. The comb 13 is arranged in the difference of elevation between the glass plates 11 and 11'.

The partition frame 2 comprises a first side jamb 21, a second side jamb 21' arranged in parallel to the first side jamb 21, a bottom rail 22 connected between the first side jamb 21 and the second side jamb 21' at the bottom, a transverse plate 25 connected between the side jambs 21 and 21' and spaced above the bottom rail 22, two positioning rods 26 and 26' respectively outwardly raised from the side jambs 21 and 21' at the top for fastening to two opposite lateral sides of the cell 5. The side jambs 21 and 21' each have a positioning groove 23 longitudinally disposed at an outer side, and respectively coupled to two vertical sidetracks 31 inside the rack 3. The bottom rail 22 has a positioning groove 221 longitudinally disposed at a bottom side in communication with the positioning groove 23 at each side jamb 21 and 21'. The second side jamb 21' has a vertical through hole 211' through which a negative electrode is inserted with a conductor and fastened to a locating block 24 between the bottom rail 22 and the second side jamb 21', forming a negative electric zone. The first side jamb 21 has a vertical through hole 211 through which a positive electrode is inserted with a conductor and extended to the positioning groove 23 adjacent to the bottom rail 22, forming a positive electric zone. A protruding index 27 is provided at the positioning rod 26' at the second side jamb 21' for guiding the installation of the cover 52 of the cell 5 into position to prevent an electric connection error. Two locating grooves 28 are provided at the front and back sides of the partition frame 2, and extended through the side jambs 21 and 21' and the bottom rail 22. A flexible gasket 29 is respectively fastened to each locating groove 28. Each locating groove 28 has two sloping ends 281 extended upwardly outwards toward the top at each side jamb 21 and 21'. After installation of the gaskets 29 in the locating grooves 28, the two distal ends of each gasket 29 are respectively forced outwards and firmly stopped at the glass plates 11 and 11'.

The rack 3 comprises two vertical tracks 31 bilaterally disposed on the inside for the positioning of the side jambs 21 and 21', a plurality of holding down elements 33 adjusted to evenly press on the pressure block 1 against the glass plates 11 and 11', symmetrical positioning portions 34 provided at two opposite peripheral side walls 32 thereof at a bottom side for positioning on the positioning unit 4, a plurality of protruding bearing portions 35 respectively formed integral with the positioning portions 34, a plurality of vertical locating grooves 36 bilaterally provided on the inside for the positioning of other members used during blotting, two receptacle portions 37 bilaterally disposed on the outside, two terminal holder plates 38 respectively inserted in the receptacle portions 37, and two banana plugs 39 respectively installed in the terminal holder plates 38. The terminal holder plates 38 each comprise two positioning grooves 381 disposed at two opposite lateral sides and respectively coupled to one receptacle portion 37, a positioning rod 382 and a bearing rod 383 horizontally extended from the top side thereof in reversed directions, and a protruding indicator 384 for recognition of polarity. The banana plugs 39 are respectively mounted on the bearing rod 383 at each terminal holder plate 38.

The positioning unit 4 comprises a recessed portion 42 at the top side wall thereof on the middle, a carrier plate 43 mounted in the recessed portion 42, a gasket 44 for positioning in the recessed portion 42 during an electrophoretic gelation operation, a plurality of locating holes 41 spaced around the recessed portion 42 for receiving the positioning portions 34 of the rack 3, two barrels 45 formed integral with the top side wall and transversely disposed at two opposite sides of the recessed portion 42, and two pivot members 47 respectively coupled to the barrels 45. The coupling blocks 45 each have a notch 46. The pivot members 47 each comprise a pivot shaft 471 respectively and axially inserted into the barrels 45, two cams 473 fixedly provided at two distal ends of the pivot shaft 471, and a finger rod 472 perpendicularly disposed on the middle and respectively extended out of the notch 46 at each barrel 45. The cams 473 each have a protruding portion 474.

The cell 5 comprises a casing 51 for holding the aforesaid parts and a buffer, and a cover 52 covered on the casing 51. The casing 51 comprises two coupling holes 511 at two opposite lateral side walls thereof. The cover 52 comprises a top handle 521, two cylindrical terminal receptacles 522 and 522' raised from the top side wall thereof at two opposite sides of the top handle 521, and a bottom constraint block 523 raised from the bottom side wall thereof for correct polarity positioning of the cover 52 on the casing 51.

Figure 7:
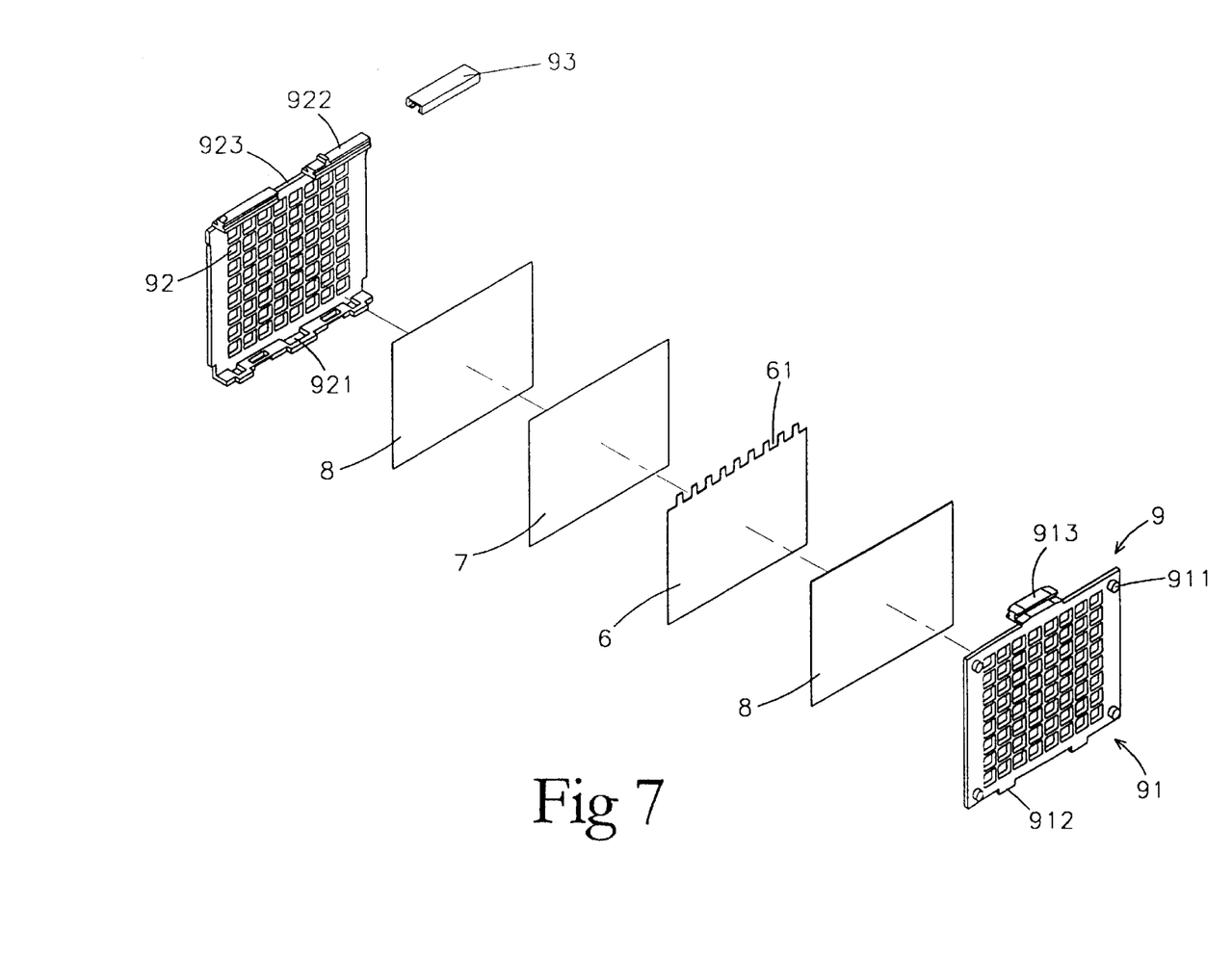
FIGS. 7, 8, 9, 10, 10A and 11 are elevational, exploded and sectional side views of the present invention, showing the apparatus arranged for blotting.
Figure 8:
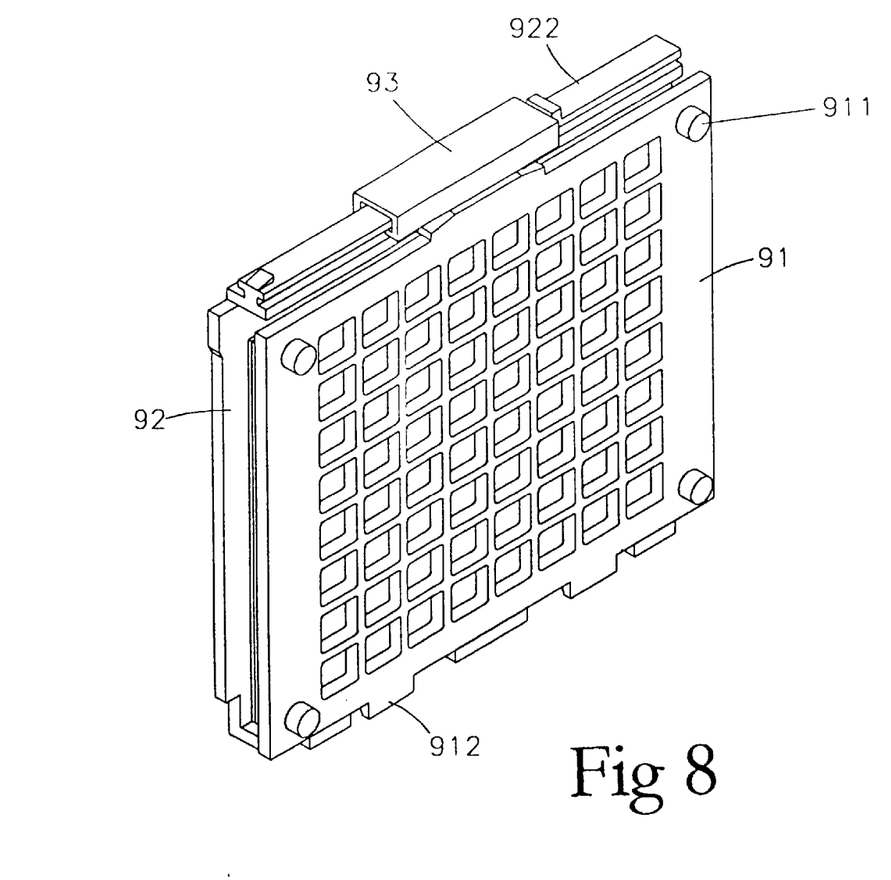

The blotting cassette 9 is comprised of two symmetrical perforated plates, namely, the first perforated plate 91 and the second perforated plate 92, and a sliding lock 93. The first perforated plate 91 comprises a plurality of foot elements 911 symmetrically raised from a back side wall thereof for supporting on a table top, a plurality of plug strips 912 downwardly extended from the bottom side thereof, and a track 913 forwardly raised from the top side thereof. The second perforated plate 92 comprises a plurality of different sizes of adjustment plug holes 921 provided at the bottom side thereof for receiving the plug strips 912 of the first perforated plate 91, a top rail 922, and a notch 923 at the top rail 922 on the middle for receiving the track 913 of the first perforated plate 91. The plug strips 912 are selectively inserted to the adjustment plugholes 912 subject to the desired pitch between the perforated plates 91 and 92. After insertion of the plug strips 912 into the adjustment plugholes 912, the track 913 is positioned in the notch 923, and the sliding lock 93 is coupled to the top rail 922 to secure the track 913 to the top rail 922 (see FIG. 7).

Figure 9:
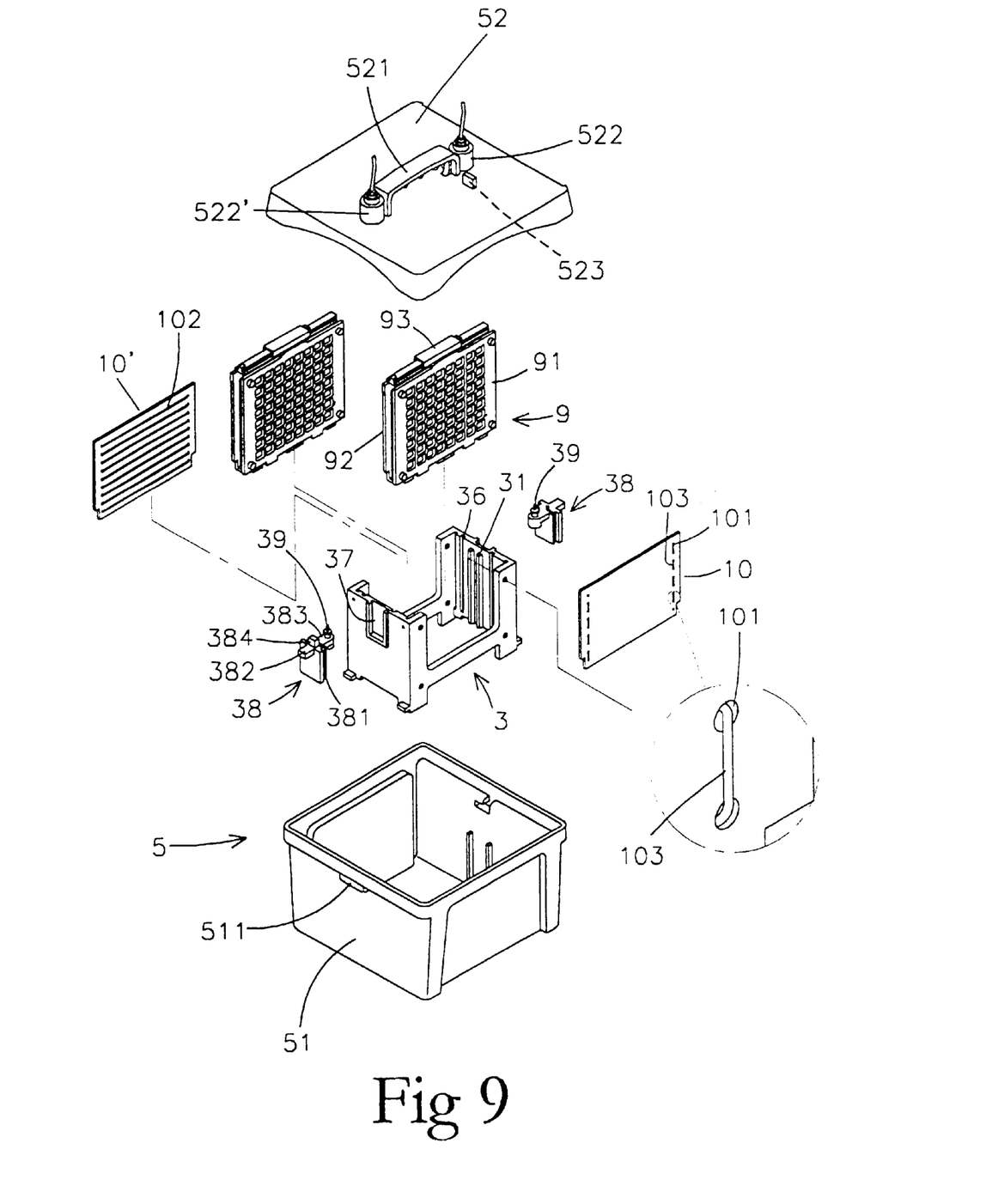
Figure 10:
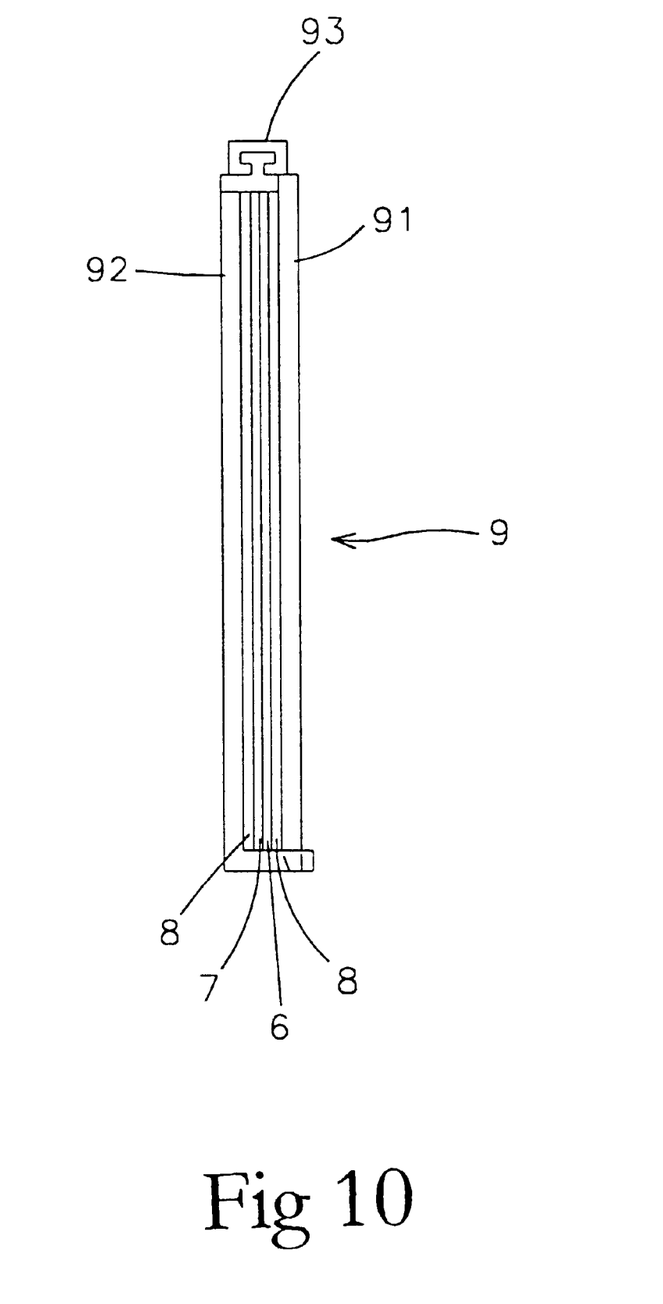
Figure 10A:
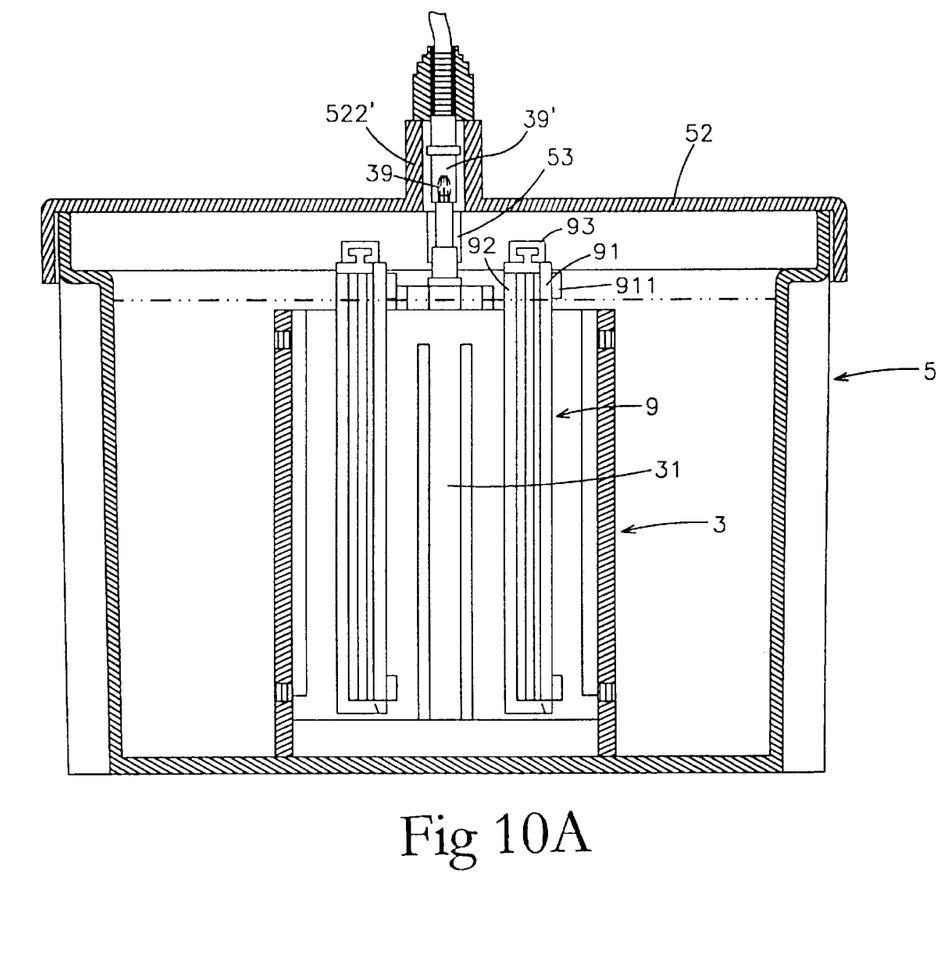
Figure 11:
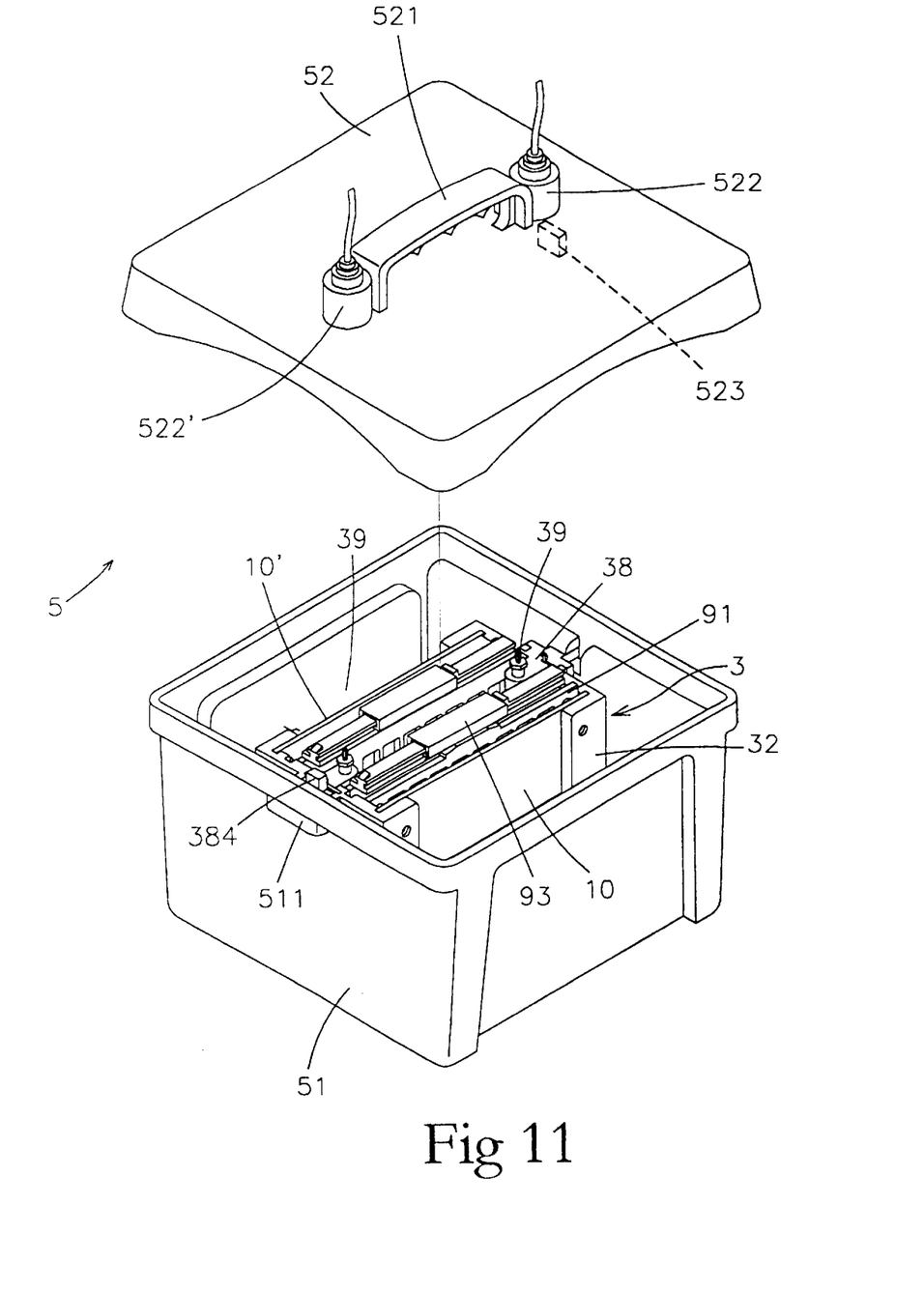

The electrode plates 10 and 10' each comprise a plurality of wire grooves 102 arranged in parallel, and a plurality of through holes 101 respectively disposed at two distal ends of each wire groove 102. Electrode conductors 103 are respectively inserted through the through holes 101, and arranged in the wire grooves 102 (see FIG. 9).

Figure 1:
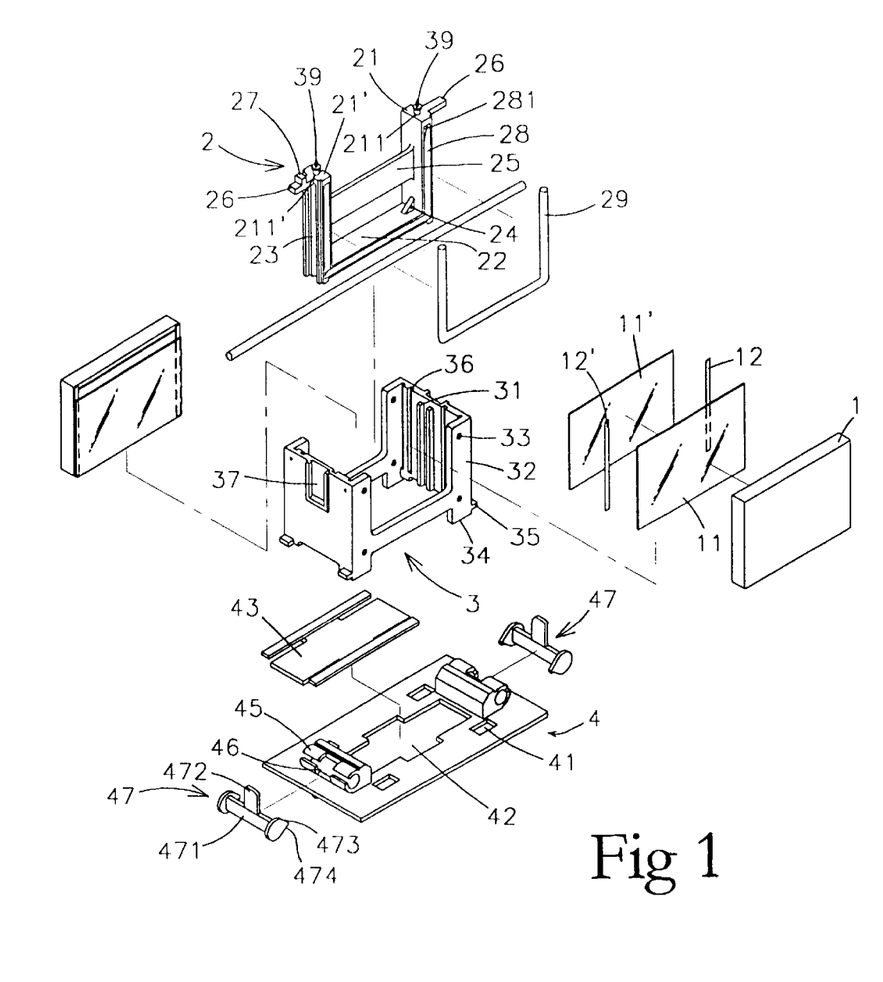
FIGS. 1, 2, 2A and 3 are exploded and sectional assembly views of a part of an electrophoretic separating and blotting apparatus according to the present invention.
Figure 2:
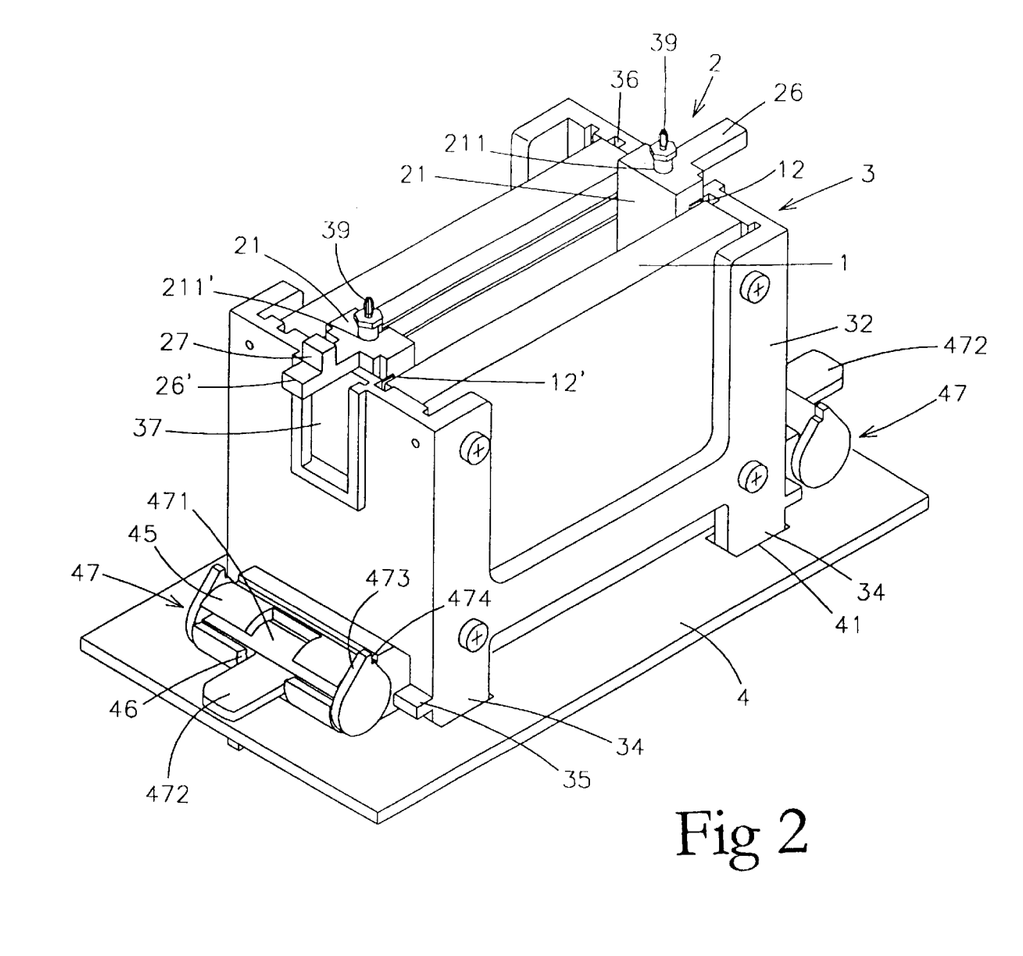
Figure 2A:
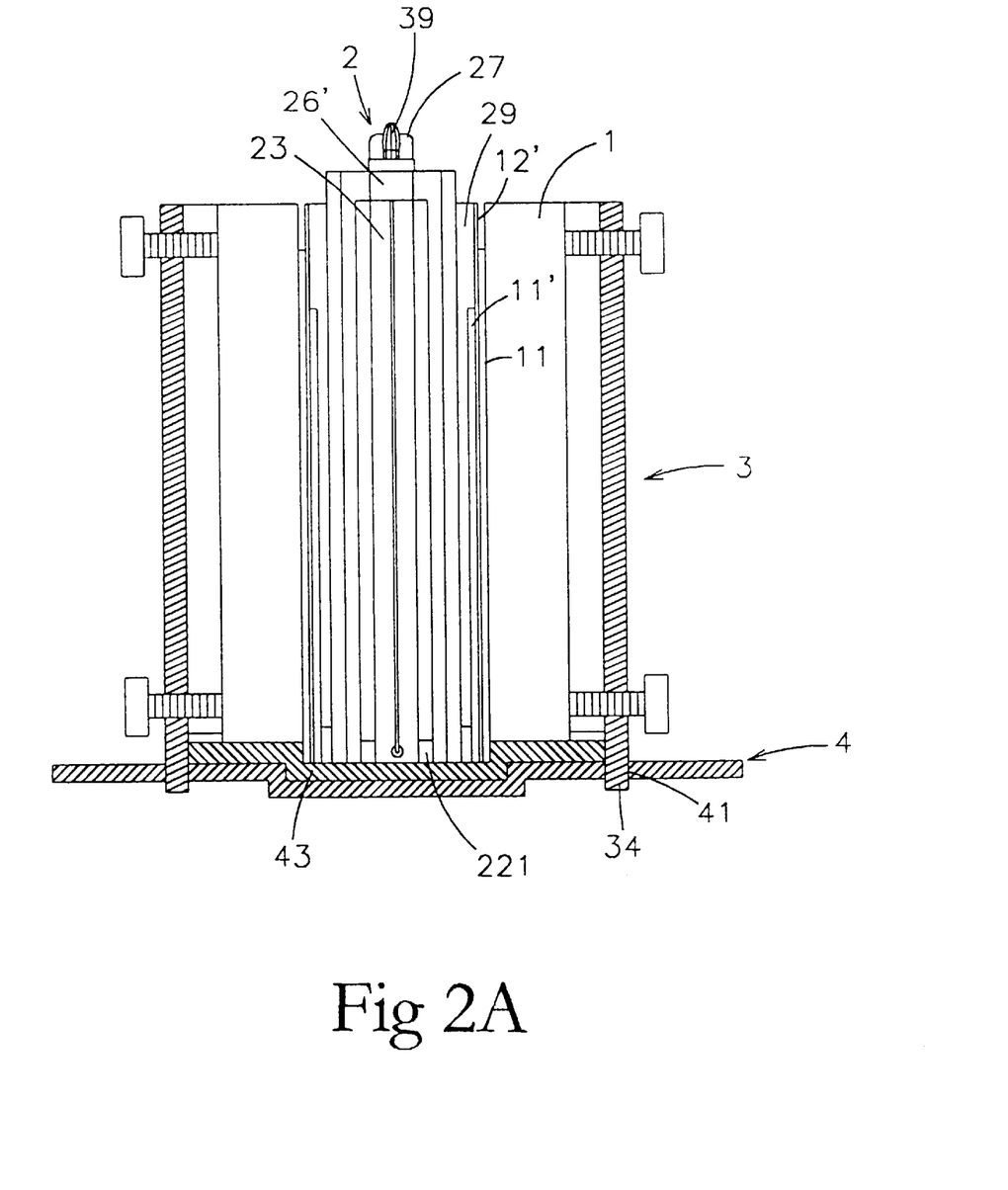
Figure 3:
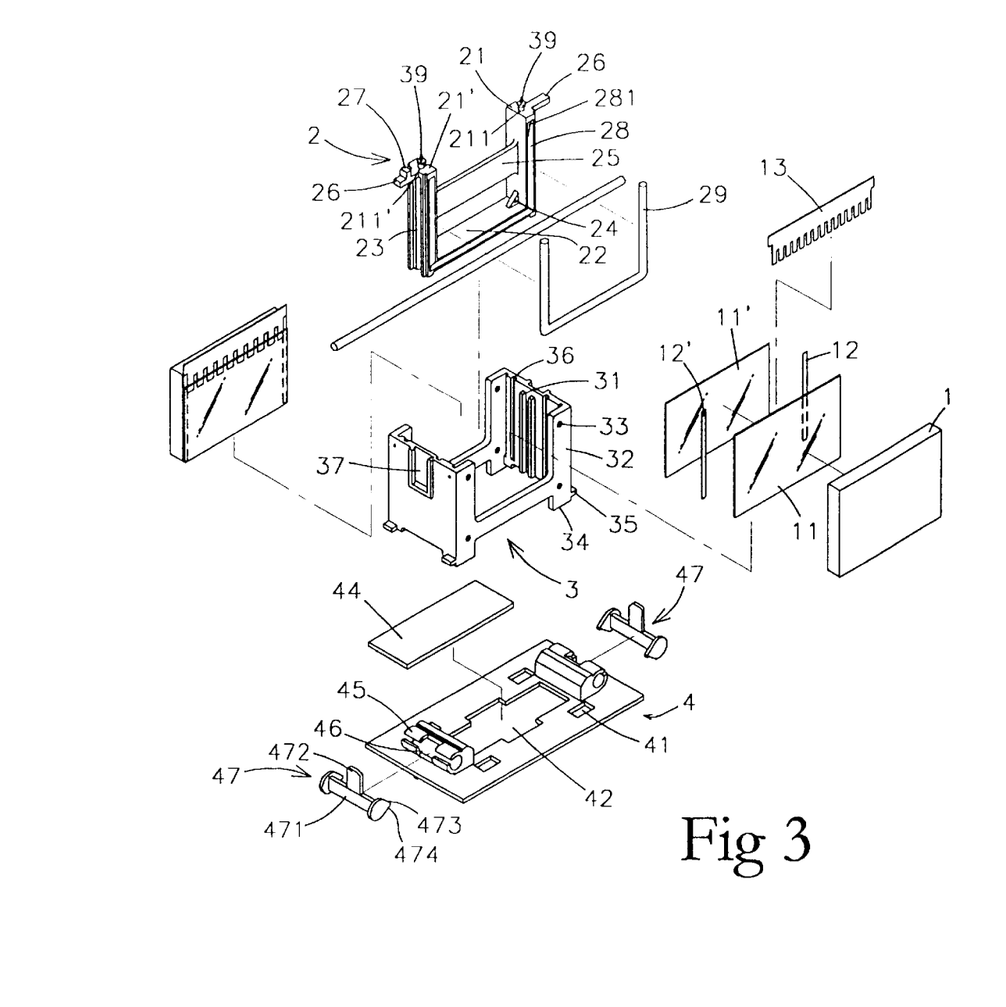
Figure 4:
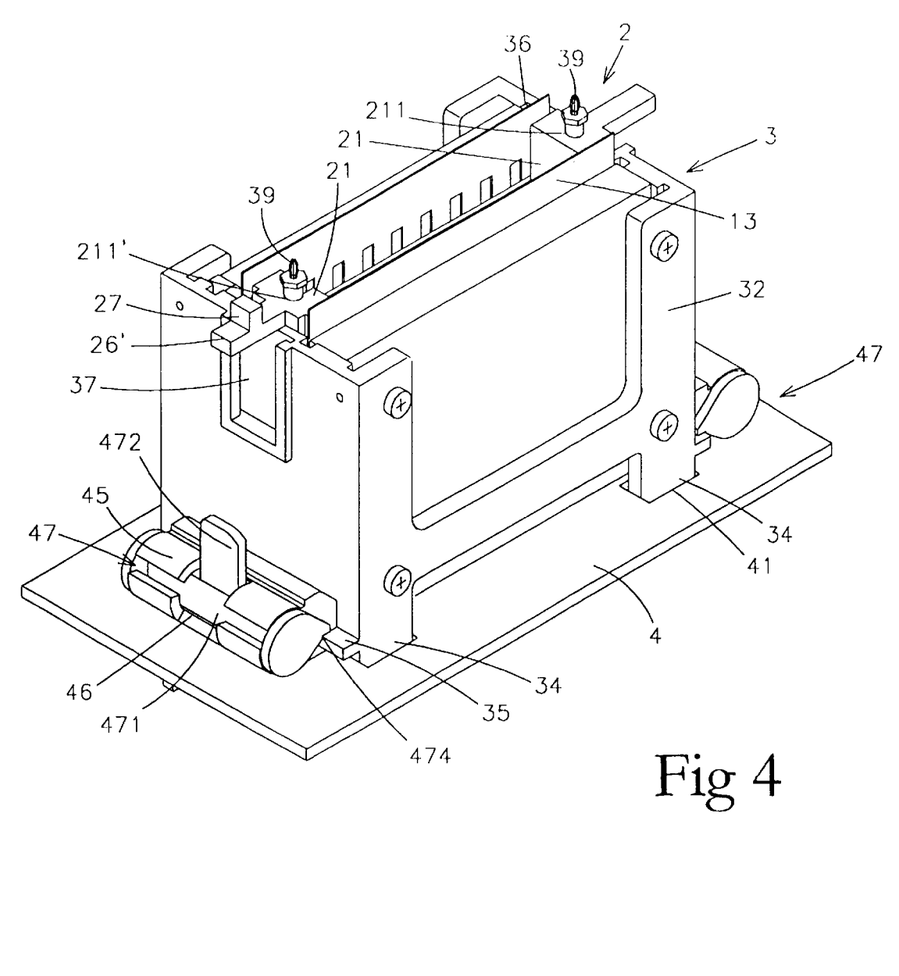
FIGS. 4 and 4A are elevational and sectional side views of a part of the present invention, showing the apparatus arranged for casting.
Figure 4A:
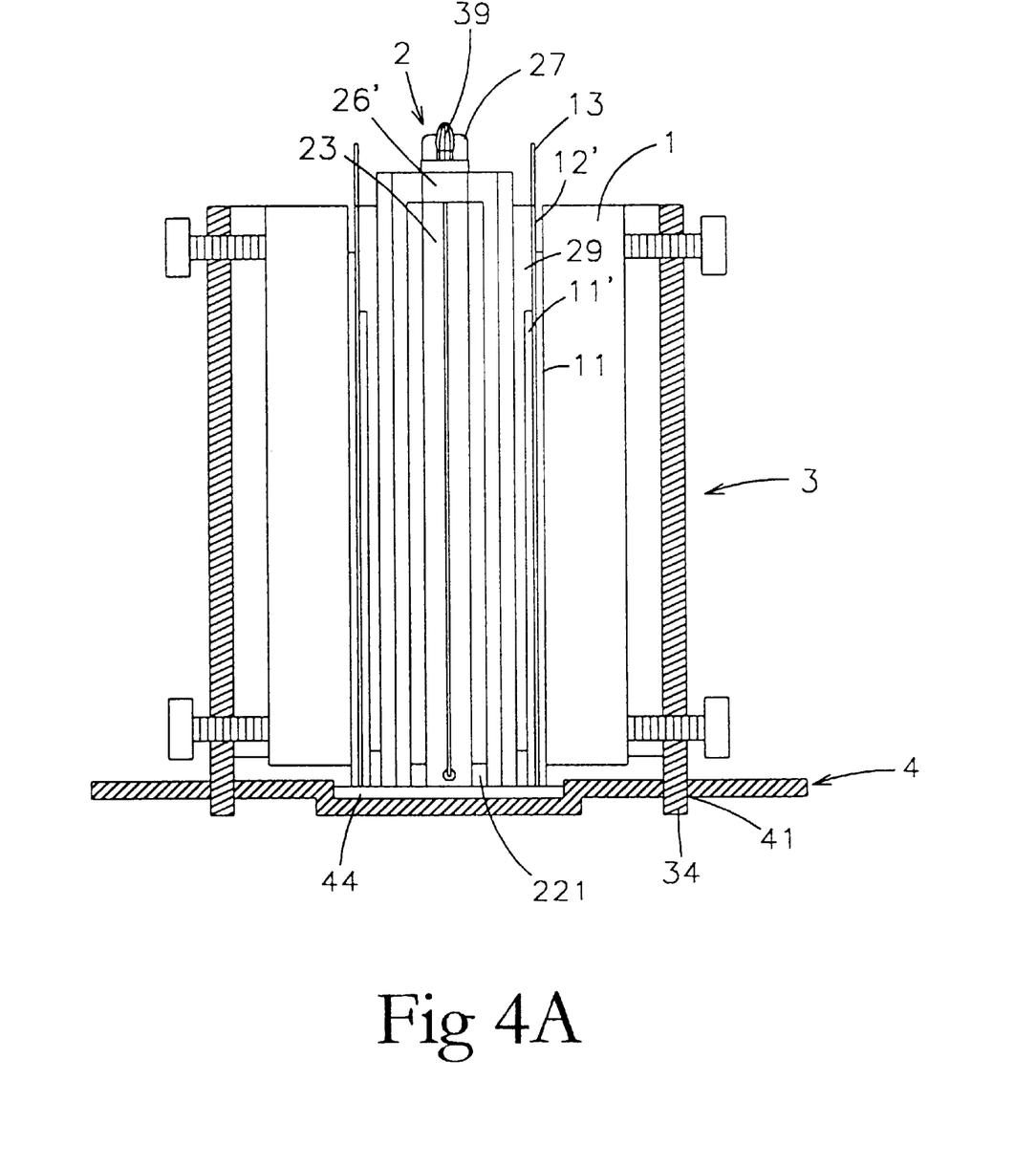
Figure 5:
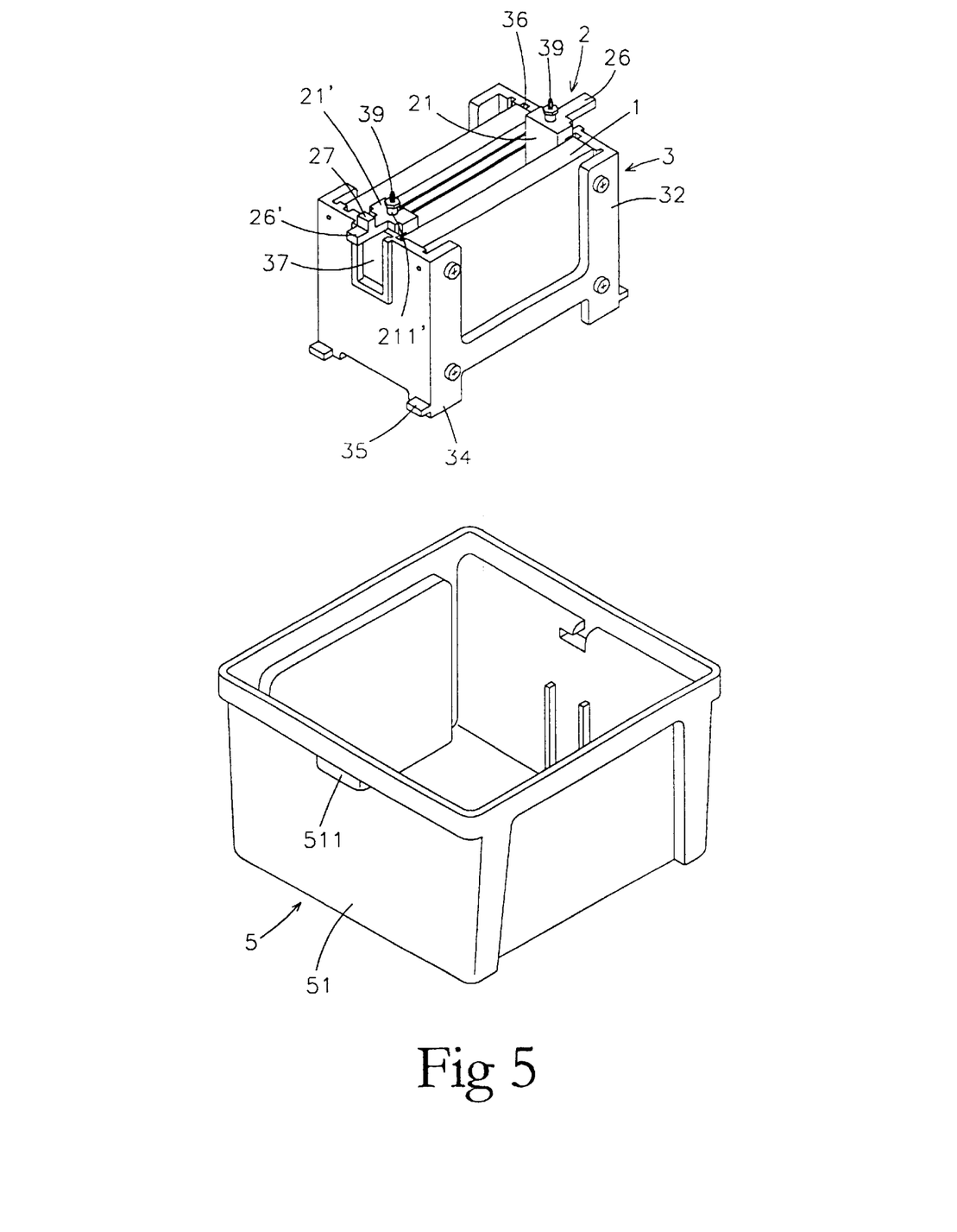
FIGS. 5, 6 and 6A are elevational, exploded and sectional side views of the present invention for the steps of loading and running.
Figure 6:
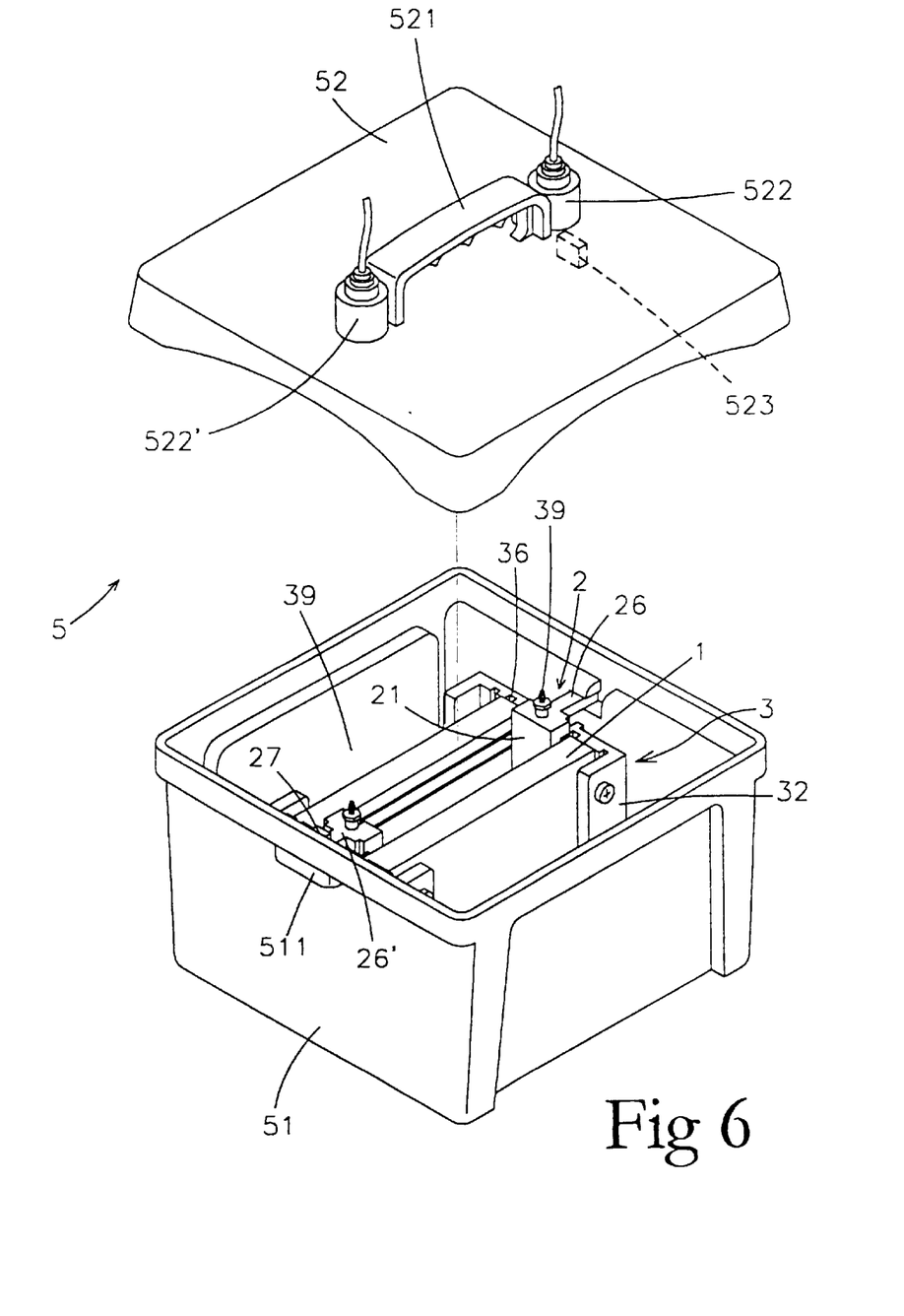
Figure 6A:
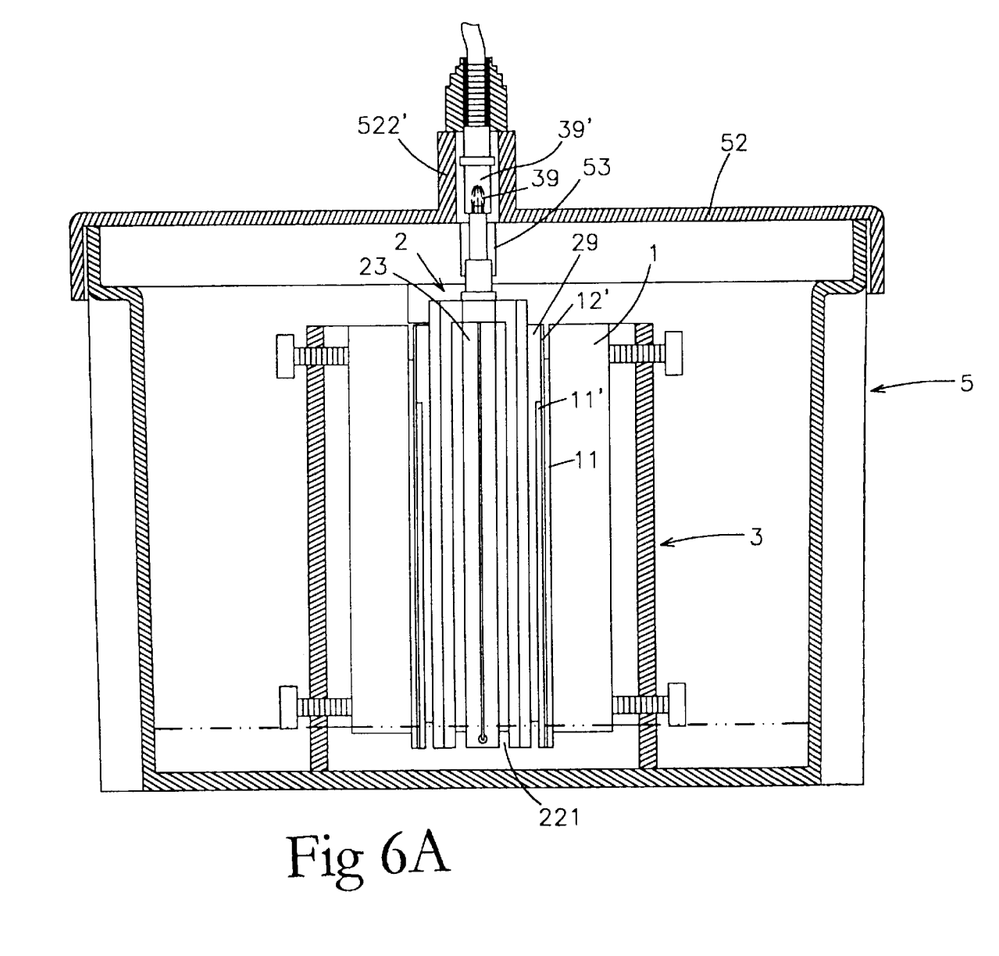

Referring to FIGS. 1, 2 and 2A, before electrophoretic gelation, all the parts are installed, and fixedly secured in place. During alignment, the carrier plate 43 is mounted in the recessed portion 42 at the positioning unit 4, then the partition frame 2 is mounted in the rack 3, and then the rack 3 with the partition frame 2 are mounted on the positioning unit 4 by plugging the positioning portions 34 into the respective locating holes 41, and then the pressure block 1 is inserted into the rack 3, and then the spacers 12 and 12' are positioned in between the two glass plates 11 and 11' and inserted with the glass plates 11 and 11' into the rack 3 between the partition frame 2 and the pressure block 1, and then the holding down elements 33 are fastened up to press the pressure block 1 against the glass plates 11 and 11', enabling the glass plates 11 and 11' to be positively supported on the gasket 29, and then the rack 3 is removed from the positioning unit 4. After removal of the rack 3 from the positioning unit 4, the carrier plate 43 is taken away (see FIGS. 3, 4 and 4A), then the gasket 44 is put in the recessed portion 42, and then the rack 3 is installed in the positioning unit 4 again, enabling the partition frame 2 and the inner area of the rack 3 to be allocated at the gasket 44, and then the finger rods 472 of the pivot members 47 are respectively turned inwards to force the protruding portion 474 of each cam 473 against the bearing portions 35 of the rack 3. At this time, a gelatin fluid is filled into the space defined between the glass plates 11 and 11' to produce a first layer of gel, and then the comb 13 is installed in the difference of elevation between the glass plates 11 and 11'. After gelation of the gelatin fluid, a second layer of gel is made, After gelation of the second layer of gel, the comb 13 is taken away, and a plurality of sample wells 61 are formed on the gel 6 at the top side (see FIG. 7). Thereafter, the rack 3 is removed from the positioning unit 4 and put in the cell 5, enabling the mounting rods 26 and 26' of the partition frame 2 to be respectively engaged into the coupling holes 511 at the casing 51 of the cell 5, and then a buffer is filled in the casing 51 and between two gels (or partition frames 2), causing the negative electrode, the gels 6, the buffer and the positive electrode form a loop. Thereafter, a sample is loaded to the wells 61 at the gel 6, then the cover 52 is covered on the casing 51 (see FIGS. 5, 6 and 6A), and then the banana plugs 39 are electrically connected, causing the sample to be arranged in order in the holes in the gel 6. After running for a certain length of time, the partition frame 2 and the rack 3 are removed from the casing 51, then the holding down elements of the rack 3 are loosened, and then the pressure block 1 and the glass plates 11 and 11' are removed from the rack 3, and then the gel 6 is taken away from the rack 3, and then the partition frame 2 is separated from the rack 3, thus the blotting operation can then be proceeded.

Referring to FIGS. from 7 through 11, before starting the blotting operation, the two pieces of filter paper 8 and the transfer membrane 7 are pre-treated to prevent the occurrence of bubbles in the filter paper 8, the transfer membrane 7 or the gel during blotting, then the transfer membrane 7 is adhered to one side of the gel 6, and then the two pieces of filter paper 8 are respectively adhered to the other side of the gel 6 and the transfer membrane 7, and then the gel 6 and the transfer membrane 7 with the filter paper 8 are fastened to the blotting cassette 9. Thereafter, the terminal holder plates 38 are respectively fastened to the insertion slots 37 at the rack 3, then the rack 3 is put in the casing 51 of the cell 5, enabling the mounting rods 382 of the terminal holder plates 38 to be respectively fastened to the coupling holes 511 at the casing 51, and then the blotting cassette 9 is put in the rack 3, and then the electrode plates 10 and 10' are respectively inserted into the vertical locating grooves 36 in the rack 3, and the banana plugs 39 are respectively connected to the electrode plates 10 and 10', and then the buffer is poured in the cell 5, and then the cover 52 is covered on the casing 51, and the blotting process is started after connection to power supply. After blotting, the rack 3 is removed from the cell 5, then the blotting cassette 9 is dismantled, and the blotted transfer membrane is obtained.

While only one embodiment of the present invention has been shown and described, it will be understood that various modifications and changes could be made thereto without departing from the spirit and scope of the invention.

What the invention claimed is:

1. An electrophoretic separating and blotting apparatus comprising:

a pressure block;

two parallel glass plates of different heights;

two spacers bilaterally retained between said glass plates;

a comb for mounting in between the difference of elevation between said glass plates;

a partition frame, said partition frame comprising a first side jamb, a second side jamb arranged in parallel to said first side jamb, a bottom rail connected between said first side jamb and said second side jamb at a bottom side, a transverse plate connected between said side jambs and spaced above said bottom rail, two positioning rods respectively outwardly raised from said side jambs at a top side for fastening to two opposite lateral sides of a cell, two locating grooves respectively provided at front and back sides thereof and extended through said side jambs and said bottom rail, and two gaskets respectively fastened to said locating grooves, said side jambs each having a positioning groove longitudinally disposed at an outer side for coupling to two vertical side tracks inside a rack, said bottom rail having a positioning groove longitudinally disposed at a bottom side thereof in communication with the positioning groove at each of said side jambs, said second side jamb having a vertical through hole through which a negative electrode is inserted with a conductor and fastened to a locating block between said bottom rail and said second side jamb to form a negative electric zone, said first side jamb having a vertical through hole through which a positive electrode is inserted with a conductor and extended to the positioning groove at said first side jamb adjacent to said bottom rail to form a positive electric zone, the positioning rod of said second side jamb comprising a protruding index for guiding the installation of a cell into position to prevent an electric connection error;

a rack, said rack comprising two vertical tracks bilaterally disposed on the inside for the positioning of the side jambs of said partition frame, a plurality of holding down elements adjusted to press on said pressure block against said glass plates, symmetrical positioning portions provided at two opposite peripheral side walls thereof at a bottom side for positioning on a positioning unit, a plurality of protruding bearing portions respectively formed integral with said positioning portions, a plurality of vertical locating grooves bilaterally provided on the inside for the positioning of blotting members, two receptacle portions bilaterally disposed on the outside, two terminal holder plates respectively inserted in said receptacle portions, and two banana plugs respectively installed in the terminal holder plates, said terminal holder plates each comprising two positioning grooves disposed at two opposite lateral sides and coupled to said receptacle portions, a positioning rod and a bearing rod horizontally extended from a top side thereof in reversed directions, and a protruding indicator for recognition of polarity;

a positioning unit, said positioning unit comprising a recessed portion at a top side wall thereof on the middle, a carrier plate mounted in said recessed portion, a gasket for positioning in said recessed portion during an electrophoretic gelation operation, a plurality of locating holes spaced around said recessed portion for receiving the positioning portions of said rack, two barrels formed integral with the top side wall and transversely disposed at two opposite sides of said recessed portion, and two pivot members respectively coupled to said barrels, said coupling blocks each having a notch, said pivot members each comprising a pivot shaft respectively and axially inserted into said barrels, two cams fixedly provided at two distal ends of said pivot shaft, said cams each having a protruding portion, and a finger rod perpendicularly disposed on the middle and respectively extended out of the notch at each barrel for turning by hand to force the protruding portion of each of said cams against the bearing portions of said rack;

a cell for receiving said rack and said partition frame in said rack, said cell comprising a casing, and a cover covered on said casing, said casing comprising two coupling holes at two opposite lateral side walls thereof for the positioning of the mounting rods of said rack, said cover comprising a top handle, two cylindrical terminal receptacles at two opposite sides of said top handle, two electric terminals respectively installed in said terminal receptacles, and a bottom constraint block raised from a bottom side wall thereof for correct polarity positioning of said cover on said casing;

a blotting cassette, said blotting cassette comprising a first perforated plate, a second perforated plate, and a sliding lock, said first perforated plate comprising a plurality of foot elements symmetrically raised from a back side wall thereof for supporting on a table top, a plurality of plug strips downwardly extended from a bottom side thereof, and a track forwardly raised from a top side thereof, said second perforated plate comprising a plurality of different sizes of adjustment plug holes provided at a bottom side thereof for receiving the plug strips of said first perforated plate, a top rail, and a notch at said top rail on the middle for receiving the track of said first perforated plate, said sliding lock being coupled to the top rail of said first perforated plate to secure the track of said second perforated plate to the top rail of said first perforated plate; and two electrode plates respectively inserted into said rack, said electrode plates each comprising a plurality of wire grooves arranged in parallel, and a plurality of through holes respectively disposed at two distal ends of each of said wire groove for receiving electrode conductors.

2. The electrophoretic separating and blotting apparatus of claim 1 wherein the locating grooves at the front and back sides of said partition frame each have two sloping ends extended upwardly outwards toward the topmost edge of each of said side jambs to force the ends of the respective gaskets outward against said glass plates.

3. The electrophoretic separating and blotting apparatus of claim 1 wherein the gaskets, which are installed in said partition frame, are flexible.

* * * * *